United States Patent
Petersen

(10) Patent No.: US 10,383,432 B2
(45) Date of Patent: Aug. 20, 2019

(54) INTERDENTAL BRUSH AND DIAGNOSTIC METHOD WITH SAID INTERDENTAL BRUSH

(71) Applicant: SOLO-MED GmbH, Trier (DE)

(72) Inventor: Ralf Petersen, Bernburg (DE)

(73) Assignee: SOLO-MED GmbH, Trier (DE)

( * ) Notice: Subject to any disclaimer, the term of this patent is extended or adjusted under 35 U.S.C. 154(b) by 0 days.

(21) Appl. No.: 15/496,617

(22) Filed: Apr. 25, 2017

(65) Prior Publication Data

US 2017/0311705 A1   Nov. 2, 2017

(30) Foreign Application Priority Data

Apr. 30, 2016   (DE) .................. 10 2016 005 332

(51) Int. Cl.
| | |
|---|---|
| A46B 3/18 | (2006.01) |
| A46B 9/04 | (2006.01) |
| A46B 15/00 | (2006.01) |
| A61B 5/00 | (2006.01) |
| A61C 15/00 | (2006.01) |

(52) U.S. Cl.
CPC .................. *A46B 3/18* (2013.01); *A46B 9/04* (2013.01); *A46B 15/0085* (2013.01); *A61B 5/4547* (2013.01); *A61B 5/4552* (2013.01); *A61C 15/00* (2013.01); *A46B 2200/108* (2013.01); *A46B 2200/405* (2013.01)

(58) Field of Classification Search
CPC ......... A46B 3/18; A46B 9/04; A46B 15/0085; A46B 15/00; A46B 15/4552; A46B 2200/108; A46B 2200/405
USPC .......................................................... 433/215
See application file for complete search history.

(56) References Cited

U.S. PATENT DOCUMENTS

| | | | | |
|---|---|---|---|---|
| 5,699,578 A | * | 12/1997 | Dumler | A46B 3/18 |
| | | | | 132/321 |
| 8,132,579 B1 | * | 3/2012 | Wien | A61C 15/042 |
| | | | | 132/321 |
| 2008/0216267 A1 | | 9/2008 | Chu | |

FOREIGN PATENT DOCUMENTS

DE   9313034   12/1993

\* cited by examiner

*Primary Examiner* — Heidi M Eide
*Assistant Examiner* — Mirayda A Aponte
(74) *Attorney, Agent, or Firm* — Volpe and Koenig, P.C.

(57) ABSTRACT

An interdental brush (1) with a handle (2) and a brush head (3), wherein the brush head (3) includes a wire element (4), which extends from the handle (2) to a free end (5) and to which bristles (7) are attached, which decrease in length towards the free end (5) of the wire element (4) in at least one section, and wherein a bristle-free section (8) is formed at the free end (5) of the wire element (4).

3 Claims, 4 Drawing Sheets

INTERDENTAL BRUSH AND DIAGNOSTIC METHOD WITH SAID INTERDENTAL BRUSH

INCORPORATION BY REFERENCE

The following documents are incorporated herein by reference as if fully set forth: German Patent Application No. 102016005332.1, filed Apr. 30, 2016.

BACKGROUND

The invention describes an interdental brush with a handle and a wire element to which bristles are attached, and which extends from the handle to a free end.

Such interdental brushes are typically used to clean interdental spaces. For this purpose, bristles on the bristle head essentially form the shape of a cylinder or cone, for example. The bristle head is inserted into the interdental space and moved back and forth. The width of interdental spaces can vary greatly from person to person and even from tooth to tooth of the same person. For this reason, interdental brushes usually come with different size bristle heads, so that there is a suitable interdental brush for each interdental space. Interdental brushes are available as hygiene products to be used by the user himself, or as medical products to be used by a dentist.

If spaces between teeth are not regularly cleaned with an interdental brush, bacteria build up in these spaces, potentially leading to gingivitis, periodontitis or tooth decay. This also occurs because a regular toothbrush is not sufficient to clean such interdental spaces. Narrow interdental spaces pose the greatest risk of disease. A narrow interdental space means both teeth on either side of the space touch each other at at least one point of contact.

Such bacterial diseases occurring in interdental spaces, especially chronic gingivitis, can be diagnosed using interdental brushes. There are diagnostic interdental brushes with cylindrical brush heads for this purpose, which are inserted into the interdental space. When inserting the brush, the bristles are bent slightly towards the handle by the teeth and gums. When extracting the interdental brush, the bristles bend the other way. This spring effect caused by the bristles triggers bleeding in diseased tissue.

However, this diagnosis only works if the bristles are long enough to reach the diseased tissue, for example in the junctional epithelium. The bristles should also not be so long that they cannot bend the other way on extraction. If this is the case, they will remain bent towards the handle and will not trigger bleeding even if the tissue is diseased. If the bristles are far too long, the interdental brush cannot be inserted into the interdental space.

Since it is not clear from the outset which brush head diameter has the suitable bristle length, there are diagnostic kits with several interdental brushes, 12 for example, with increasing brush head diameters.

Starting with the interdental brush with the smallest head diameter, the head diameter should be gradually increased until gums start to bleed, or until the largest brush is used and no bleeding has occurred.

Depending on the size of the interdental space and experience of the dentist, it may still be necessary to try a large number of different brushes. This is time-consuming and requires using numerous interdental brushes.

SUMMARY

Therefore, the purpose of the invention is to create an interdental brush and a diagnostic method enabling a simple, fast and reliable diagnosis of diseases in interdental spaces.

This purpose is achieved by an interdental brush with one or more features of the invention, and a diagnostic method with one or more features of the invention.

Further advantageous features of the invention are described below and in the claims.

The interdental brush according to the invention is characterised in that the bristles decrease in length towards the free end of the wire element, in at least one section.

The advantage consists in the fact that the interdental brush according to the invention comprises bristles of varying lengths. Therefore, it is only necessary to use this one interdental brush to diagnose diseases in interdental spaces. The bristle length gradually increases from the free end to the handle. When inserting the interdental brush according to the invention into an interdental space, the bristle length thus gradually increases within this space. When extracting the interdental brush, usually one of the bristle lengths will have fit exactly into this interdental space. These matching bristles, at the very least, then bend the other way and trigger bleeding in diseased tissue. Regardless of the size of the interdental space, at least one bristle length will always fit. This means that diseased tissue can be positively diagnosed in virtually all cases.

Vice versa, when gums do not bleed, it is virtually assured that disease can be ruled out. Up to now, when using any interdental brush, there was always the question of whether a bristle length was suitable.

Now only one interdental brush is required for a reliable diagnosis. It is much easier to use and more fail-safe in its diagnosis.

When using a conventional interdental brush, it can be difficult to penetrate an interdental space, especially in the case of larger bristle lengths. A brush can only enter an interdental space by exerting pressure, due to the resistance of the bristles. This resistance is all the greater the longer the bristles are in relation to the interdental space. If the resistance is too great, the wire element may bend and the interdental brush cannot enter into the interdental space being examined.

On the interdental brush according to the invention, a bristle-free section is now formed at the free end of the wire element, that is to say the bristle head. This bristle-free section serves as an aid for inserting the interdental brush. Since this section does not have any bristles, this region of the wire element can be inserted into any interdental space almost effortlessly, until the first bristles come into contact with the teeth and gums. Only then is resistance created, which must be overcome by exerting pressure. Yet by then the interdental brush has been firmly guided into the interdental space. Serving as an additional guide, a loop, to be subsequently explained in more detail, is able to aid the process, as it comes into contact with the teeth on both the left and right side. The wire element can no longer bend as a result of the pressure exerted on the interdental brush; rather it follows the bristle-free section into the interdental space.

Consequently, the interdental brush according to the invention can be inserted in a much easier and more positive manner. In general, the interdental brush enables a quick, easy and reliable diagnosis of gum diseases, such as chronic gingivitis.

The bristles are fixed to the wire element. Therefore, the wire element is suitably designed for mounting the bristles. Different from what the name suggests, it can be made of either a plastic or metal wire, for example. The bristles could be attached to a plastic wire element in an in-mould process, for instance.

In an advantageous variant of the invention, the wire element has two strands twisted together, which hold the bristles between them and which are connected to one another at the free end. A metal wire is most suited to this purpose. The wire element thus has a rounded or round end. This prevents any harm or damage to gums and/or teeth being caused by sharp edges present on the insertion end.

It can be especially advantageous if the two strands are formed from a single piece of wire. In this case, the wire element can be made by simply folding or bending, then twisting a piece of wire.

To ensure the brush can be firmly guided into the interdental space, it can be advantageous if the loop or bristle-free section extends over at least a length of one full turn of the twisted strands around each other.

In a particularly advantageous variant of the invention, the twisted strands form a bristle-free loop in the bristle-free section. This loop essentially allows the interdental brush to be guided into the interdental space along the tooth surface, thereby preventing the interdental brush from twisting both during and after its insertion into an interdental space. The loop also prevents the opposite papilla of an interdental space from being harmed. In addition, the loop reassures the patient that he cannot be hurt. In this respect the interdental brush itself contributes to calming the patient. By reducing the extent to which the brush is able to move, the interdental brush is even easier to use.

It is convenient if the bristle-free loop has a maximum external diameter which is larger than an external diameter of the twisted strands in the region of the bristles. This way it is ensured that the interdental brush can be safely guided into the interdental space.

It can be especially advantageous if the loop extends over at least a length of one full turn of the twisted strands around each other. The dimensions of the bristle-free section, and potentially of the loop, arise as a result of these geometrical requirements.

In a convenient design of the invention, the length of the bristle-free section is at least 1 mm, preferably at least 1.5 mm, and best of all at least 2 mm. This length is sufficient to ensure a safe insertion.

In principle, the outer contour of the brush head formed by the free bristle ends is not essential for the invention, as long as the length of the bristles decreases towards the free end in at least one section. The outer contour could have either a square, triangular or round cross section, for example.

It is particularly advantageous if the bristle length is smallest at the free end, so that it is easier to insert the brush into an interdental space.

In a particularly advantageous variant of the invention, the bristles define an outer contour tapering off towards the free end with their free bristle ends. In such a design, the bristle length steadily alters in equal steps, enabling an accurate and specific diagnosis.

In a preferred design of the invention, this outer contour is conical or cone-shaped. The cross section of the brush head is therefore circular, whereby the bristle lengths are equal across the wire element in every radial direction. When inserting such a conical interdental brush, there is no preferred orientation which must be observed, which facilitates its use.

On the other hand, an interdental brush with a cross section in the form of an acute-angled triangle could be more advantageous for very narrow interdental spaces.

Since the interdental space is only a few millimeters long and no length of the interdental brush should extend out onto the other side of the tooth, the length of the wire element, that is to say the brush head, is generally limited. A steep opening angle of the outer contour of the bristles is beneficial to enable as many bristles of different lengths as possible to be positioned on this limited length.

In a particularly advantageous variant of the invention, the bristle-free section protrudes from a theoretical extension of the outer contour towards the wire element. Thus, a sufficiently steep outer contour is ensured so that the lengths of bristles between individual bristles are not merely marginally different.

An interdental brush according to the invention with a loop at the open end of the brush head only has two possible spatial orientations in which it can be inserted into an interdental space. It is therefore advantageous if the handle has a means of indicating the preferred orientation.

For example, there could be a marking on the handle, which indicates which way the loop is spatially oriented. This marking could be an imprint, for instance.

However, as another example, the handle could have an oval grip, or a region of grip which is flattened in the same direction as the loop. Thus, the orientation of the loop could be discerned purely by touch.

It is especially practical to provide an interdental brush kit with at least two interdental brushes according to the invention, whereby the, or one bristle-free loop at the free end of the wire element of each of the at least two interdental brushes is oriented in the same direction as the corresponding handle. This ensures that each interdental brush has the same orientation.

Furthermore, a new, efficient diagnostic method can be employed with the interdental brush according to the invention, which is also an integral part of the invention.

In this diagnostic method, an interdental brush according to the invention is inserted into a narrow interdental space between a point of tooth contact and junctional epithelium, and it can be detected whether bleeding of the junctional epithelium is triggered.

Due to the advantages of the invention described above, only one interdental brush is ever required for each interdental space in this diagnostic method. In addition, the diagnostic method according to the invention demonstrates a sensitivity of almost 100%, whilst simultaneously demonstrating a very good selectivity of also almost 100%. This means that bleeding virtually always points to the presence of disease, and lack of bleeding virtually always rules out the presence of disease.

Diseases in interdental spaces can be diagnosed quickly and reliably by using this method.

In one development of the diagnostic method, a number of narrow interdental spaces are juxtaposed with a number of narrow interdental spaces which bleed when provoked. For each interdental space, for example, it is recorded whether it is narrow, whether there is space closure and whether disease is present. This ratio then indicates how many interdental spaces are diseased. For practical purposes this diagnosis is issued with a date and repeated regularly. It can be especially practical to record the diameter or the bristle length that triggered the bleeding.

In this way dental and disease history can be generated. It can be deduced from this history when space closure between two neighbouring teeth has occurred and if and when disease has subsequently arisen in this interdental space.

Furthermore, it is possible to generate a predictive diagnosis on the basis of this history. Due to previous time periods between a space closure and the occurrence of a disease, the time of disease can be predicted on the basis of further space closures. This newly occurring disease can be subsequently counteracted by targeted treatment.

To this end, it may be practical to regularly clean interdental spaces which bleed when provoked using an interdental brush which has an outer contour with a uniform cross section, for example, which has a cylindrical or prismatic outer contour of the bristles. In this case, it is possible to distinguish the outer contour by the free ends of the bristles.

A further development of the diagnostic method according to the invention can include re-examinations at predetermined intervals to check whether bleeding is triggered in the regularly cleaned interdental spaces. For this purpose, an interdental brush according to the invention is used once more.

For those interdental spaces which bleed when provoked, a new suitable bristle diameter is selected for the purposes of regular cleaning, and is usually larger than the previous one. An example of when this may be necessary is a reduction of inflammation-induced swollen gums, resulting in the interdental space becoming wider again.

The invention further encompasses the use of an interdental brush according to the invention for a previously described diagnostic method, as well as the manufacture of an interdental brush according to the invention.

BRIEF DESCRIPTION OF THE DRAWINGS

The invention is subsequently explained in more detail with reference to the accompanying drawings.

DETAILED DESCRIPTION OF THE PREFERRED EMBODIMENTS

Figure 1:
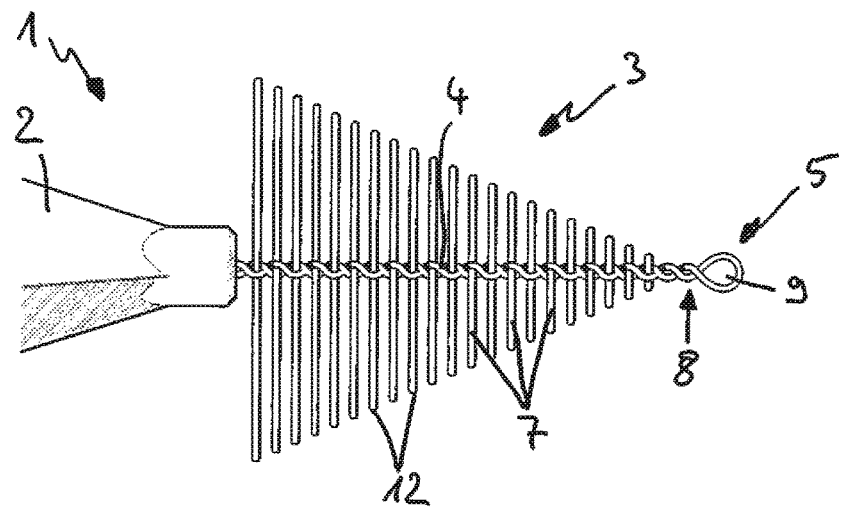
FIG. 1: shows a side view of an interdental brush according to the invention.

FIG. 1 shows an interdental brush according to the invention as a whole designated with 1. The interdental brush has a handle 2 and a brush head 3.

The shape of the handle 2 does not play an essential role in the invention, which is the reason why it is shown either only party or not at all in FIGS. 1 to 13.

In principle, the handle 2 can have any shape which enables good manual use. Particularly cylindrical rods with hexagonal or octagonal cross sections have proved successful. These are almost round, are comfortable to grip and can be more easily secured against twisting due to the edges.

In the example, the brush head 3 is positioned coaxially on the handle 2. The brush head 3 can also be positioned at an angle to the longitudinal axis of the handle, making it easier to use on molars.

The brush head 3 has a wire element 4 which is attached to the handle 2 on one side and on the other side has a free end 5.

In the example, the wire element 4 is formed out of metal wire, which is made of two strands 6, which are twisted together. The bristles 7 are kept in place in-between the twisted strands 6. At the free end 5 of the wire element 4, there are no bristles 7 in a bristle-free section 8.

The two strands 6 are connected to each other at the free end 5, where they form a bristle-free loop 9. The two strands 6 are preferably formed from one piece, whereby the loop 9 is formed initially by a bend in the middle of a wire in order to subsequently twist the two strands 6 together with the bristles 7.

The bristle length steadily decreases towards the free end 5 of the wire element 4. The free bristle ends 12 thus form a cone-shaped or conical outer contour 10 tapering off towards the free end 5 of the wire element 4.

Figure 2:
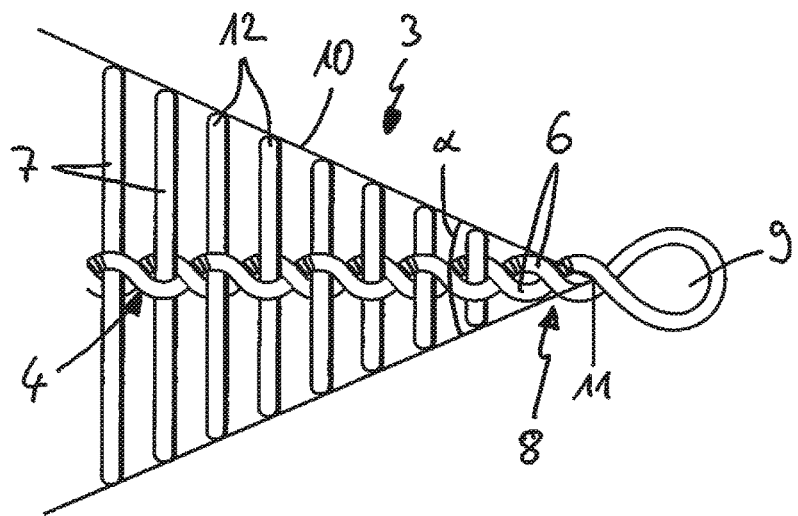
FIG. 2: shows a detailed view of the bristle-free region of the interdental brush of FIG. 1 with length specifications.

FIG. 2 illustrates a theoretical extension of the outer contour 10 up to the wire element 4, that is, to the geometric tip 11 of the cone. As can be easily seen, the bristle-free section 8 protrudes beyond this tip 11 in an axial direction. This geometric condition is important for the invention.

Figure 3:
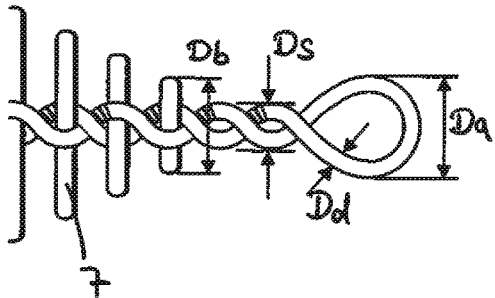
FIG. 3: shows a detailed view of the bristle-free region of the interdental brush of FIG. 1 with diameter specifications.

In FIG. 3, it can be seen that the bristle-free loop 9 has a maximum external diameter Da which is larger than an external diameter Ds of the twisted strands 6 in the region of the bristles 7. The shortest bristles have a diameter Db which is approximately equal to the diameter Da of the loop 9. The wire diameter Dd in the example is approximately 0.25 mm.

Figure 4:
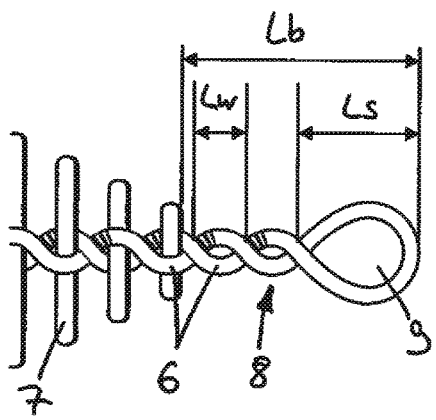
FIG. 4: shows a detailed view of the bristle-free region of the interdental brush of FIG. 1 with marked outer contour.

FIG. 4 shows that the axial length Lb of the bristle-free section 8 is longer than the length Lw of one full turn of the twisted strands 6 around each other. Also, the axial length Ls of the loop 9 is longer than the length Lw of one turn in the example.

The total length Lb of the bristle-free section 8 is directly dependent on the opening angle A of the outer contour 10 of the bristles 7, since the condition that the bristle-free section 8 protrudes beyond the tip 11 of the outer contour 10 must be fulfilled. In the example, said total length Lb is, for instance, at least 1 mm, preferably at least 1.5 mm, and at best at least 2 mm.

Figure 5:
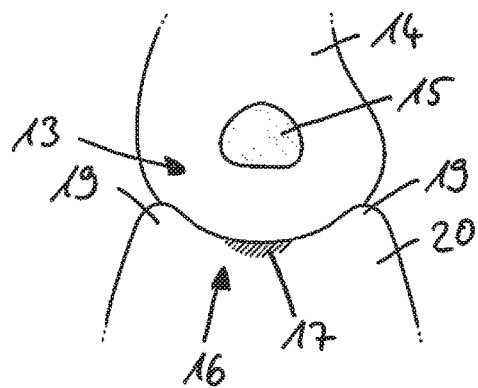
FIG. 5: shows a schematic representation of an interdental space.

FIG. 5 shows a schematic representation of a cross section through a narrow interdental space 13 between two adjacent teeth 14. In the drawing, only the rear tooth 14 can be seen, since the front tooth, which is not shown, would obscure the interdental space 13. The two teeth touch each other at an indicated point of contact 15. The depicted interdental space 13 is therefore a narrow interdental space by definition. In the middle of the col 16, an inflammation 17 is indicated.

In order to diagnose this inflammation, an interdental brush is inserted into the interdental space between the gum and point of contact.

Figure 6:
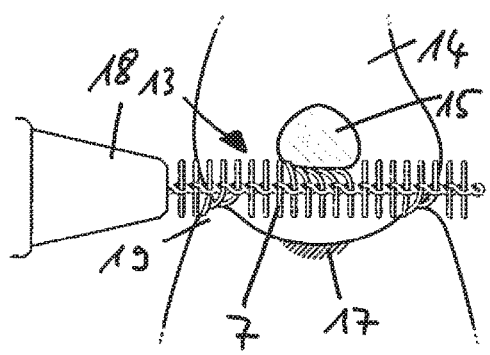
FIG. 6: shows the interdental space of FIG. 5 with an inserted cylindrical interdental brush with bristles that are too short.

In FIG. 6, an interdental brush 18 with a cylindrical outer contour according to state-of-the-art technology is shown, which has bristles 7 that are, however, too short. The bristles 7 bend namely at the papillae 19 and the point of contact 15 towards the handle 2, but do not reach the inflammation 17 in the centre of the col 16. This brush 18 does not trigger any bleeding.

Figure 7:
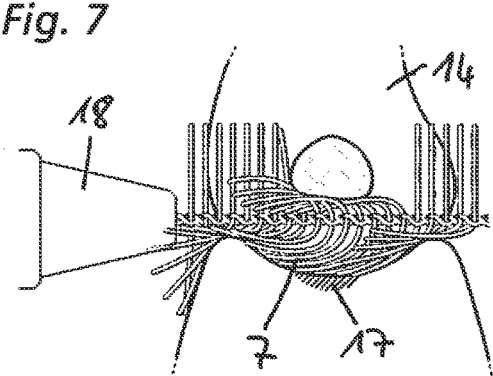
FIG. 7: shows the interdental space of FIG. 5 with an inserted cylindrical interdental brush with suitable bristles.

The opposite case is shown in FIG. 7. The bristles 7 of this cylindrical interdental brush 18 according to state-of-the-art technology are much too long, so that when extracting the interdental brush 18, the bristles 7 will not bend the other way, which also prevents bleeding from being triggered.

The inflammation cannot be diagnosed with either of these two interdental brushes.

Figure 8:
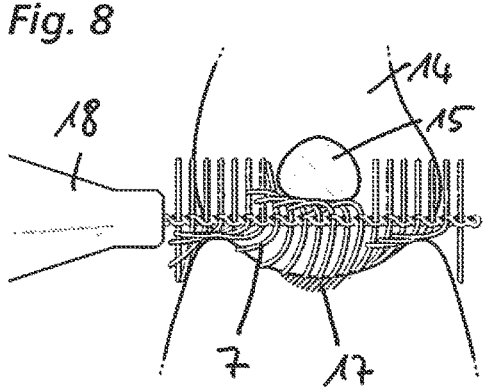
FIG. 8: shows the interdental space of FIG. 5 with an inserted cylindrical interdental brush with bristles that are too long.

The bristles 7 of the cylindrical interdental brush 18 according to state-of-the-art technology shown in FIG. 8 are the correct length. The slightly curved back bristle tips 12 reach the inflammation 17 in the centre of the col 16 well. When extracting the interdental brush, the bending effect occurs and bleeding is triggered.

Diagnosing this inflammation with cylindrical interdental brushes 18 according to state-of-the-art technology thus involves trying several such interdental brushes 18, whereby it is practical to start with a small brush diameter, which is then gradually increased.

Figure 9:
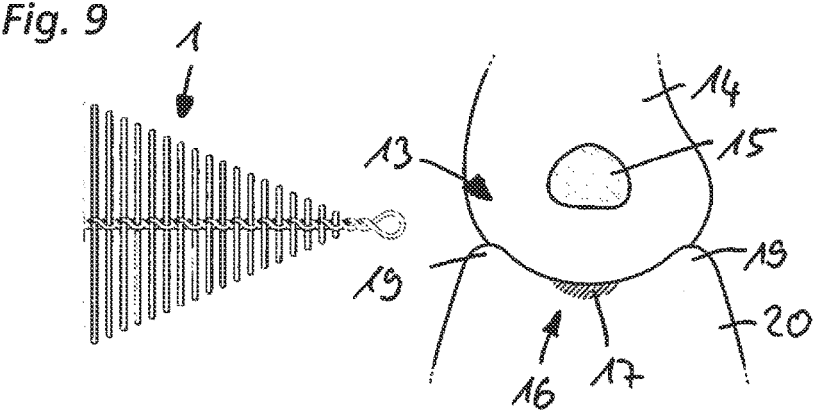
FIG. 9: shows the interdental space of FIG. 5 and an interdental brush according to the invention.

Diagnosing the inflammation becomes a lot easier with an interdental brush 1 according to the invention. FIG. 9 shows an interdental brush 1 according to the invention with a conical outer contour and a loop 9 on the bristle-free section 8, as well as the interdental space 13 already shown in FIG. 5.

This interdental brush 1 is inserted into the narrow interdental space 13 between the gum 20 and point of contact 15. With the loop 9 on the free end 5, the interdental brush 1 can be inserted particularly easily, until resistance, created by the gradually increasing length of the bristles 7 at the insertion end 21 of the interdental space 13, becomes too great.

Figure 10:
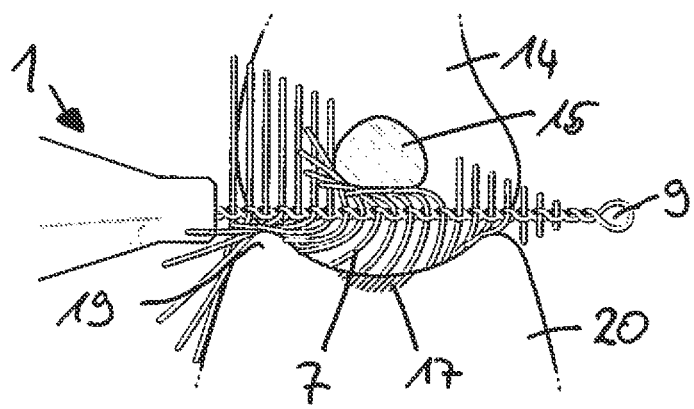
FIG. 10: shows the interdental space of FIG. 5 with an inserted interdental brush according to the invention.
Figure 11:
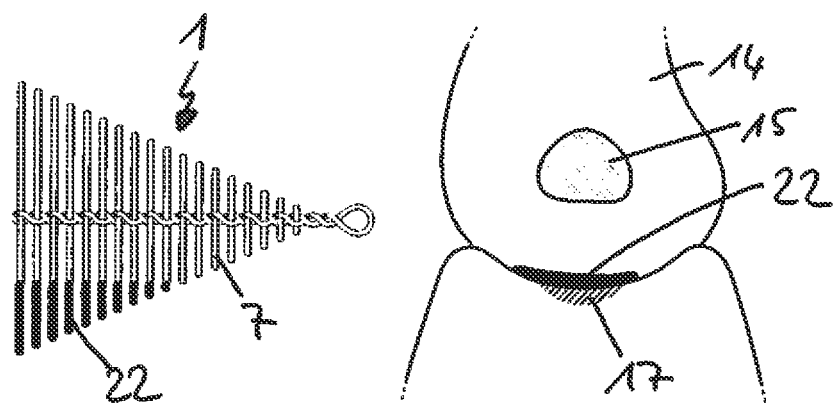
FIG. 11: shows the interdental space of FIG. 5 which has begun to bleed, with an extracted interdental brush according to the invention.
Figure 12:
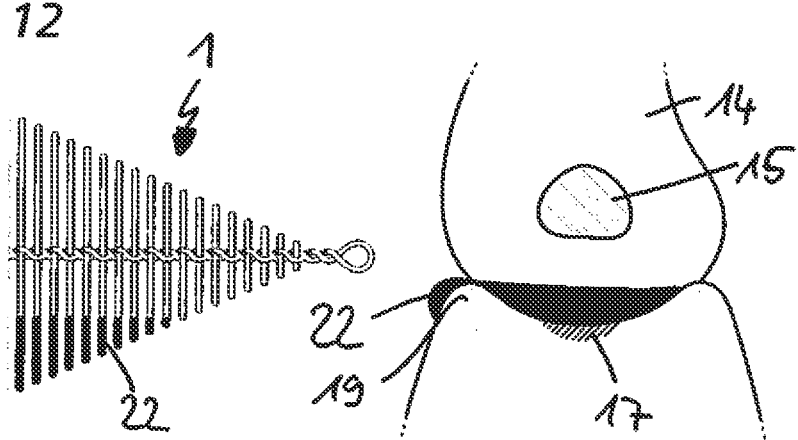
FIG. 12: shows the interdental space of FIG. 5 with visible bleeding.
Figure 13:
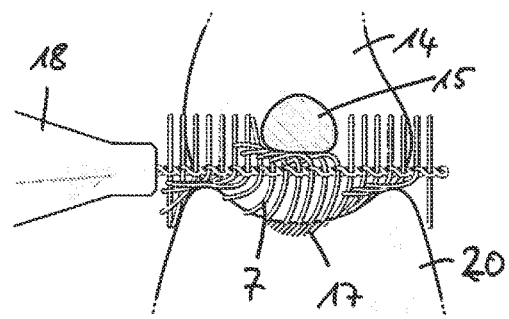
FIG. 13: shows the interdental space of FIG. 5 with an inserted cylindrical interdental brush with suitable bristles for cleaning.

As can be seen in FIG. 10, some of the bristles 7 always reach the inflamed region 17 of the col 16. When the interdental brush 1 is extracted, bleeding 22 is triggered due to the spring effect caused by the bristles 7 of the correct length bending the other way. This bleeding is indicated in FIG. 11. In the example, the inflammation 17 is located at the lowest point of the col 16, therefore the bleeding 22 is only visible from the outside if the col 16 is filled with blood 22 and the blood 22 flows over the papilla 19, as is indicated in FIG. 12.

For treatment and prevention, the interdental space 13 with a diagnosed inflammation is regularly cleaned using an interdental brush 18 with a cylindrical outer contour. The diameter of the interdental brush 18 is determined from the previously established size of the interdental space.

Figure 14:
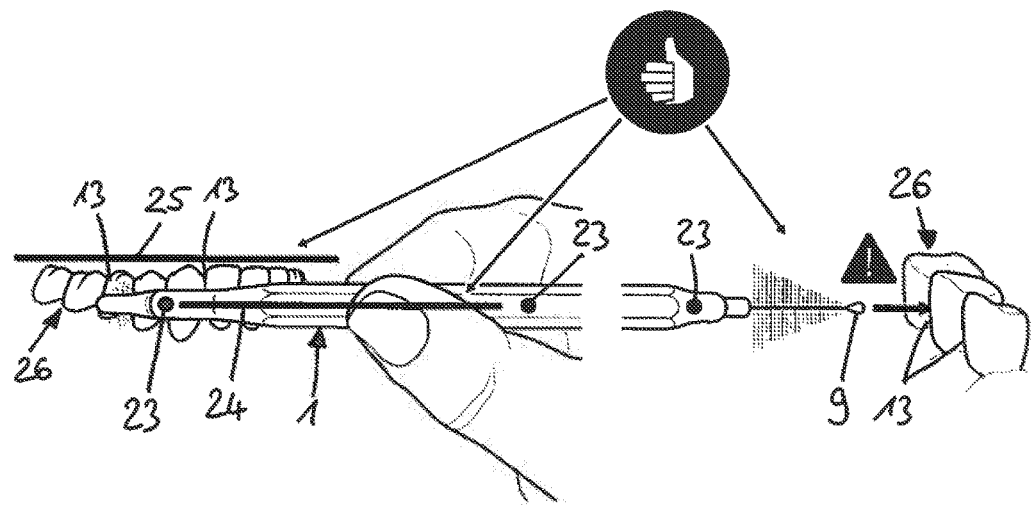
FIG. 14: shows an interdental brush according to the invention with an orientation marking on the loop.

The loop 9 at the free end of the brush head 3 serves as an aid to make it easier to insert the interdental brush 1 in narrow interdental spaces 13. As indicated in FIG. 14, the handle 2 thus features markings 23, which indicate the spatial orientation of the loop 9. In the example, this marking 23 consists of several dots which are either applied to or printed on the handle 2. If the markings 23 are in a line 24 parallel to the line 25 of a row of teeth 26, the loop 9 is oriented exactly perpendicular to the row of teeth 26, and thus in the correct orientation for insertion into an interdental space 13. The marking 23 may also feature a haptic component, so that the orientation can be deduced by feeling or touch.

An interdental brush 1 with a handle 2 and a brush head 3, wherein the brush head 3 has a wire element 4 which extends from the handle 2 to a free end 5 and to which bristles 7 are attached, which decrease in length towards the free end 5 of the wire element 4 in at least one section, and wherein a bristle-free section 8 is formed at the free end 5 of the wire element 4.

LIST OF REFERENCE NUMBERS

1 Interdental brush
2 Handle
3 Brush head
4 Wire element
5 Free end of the wire element
6 Strands
7 Bristles
8 Bristle-free section
9 Loop
10 Outer contour
11 Tip of the outer contour
12 Free bristle end
13 Interdental space
14 Tooth
15 Point of contact
16 Col
17 Inflammation
18 Interdental brush according to state-of-the-art technology
19 Papilla
20 Gum
21 Insertion end
22 Blood
23 Marking
24 Line between markings
25 Line of a row of teeth
26 Row of teeth
Da Diameter of the loop 9
Ds Diameter of the twisted strands 6
Db Diameter of the shortest bristles
Dd Diameter of one strand 6
Lb Length of the bristle-free section 8
Ls Length of the loop 9
Lw Length of one turn
α Opening angle of the outer contour 10

The invention claimed is:

1. A diagnostic method, comprising:
inserting a first, conical interdental brush having bristles that decrease in length towards a free end of the first, conical interdental brush into a narrow interdental space between a point of tooth contact and a junctional epithelium,
detecting whether a bleeding of the junctional epithelium is triggered, wherein a number of the narrow interdental spaces are juxtaposed with a number of narrow interdental spaces which bleed when provoked when the first, conical interdental brush; and
regularly cleaning using a second interdental brush the number of narrow interdental spaces which bleed when provoked using the first, conical interdental brush, the second interdental brush has a second bristle area having a second outer contour with a uniform cylindrical cross-section from a proximal end of the second bristle area to a free end of the second bristle area.

2. The diagnostic method according to claim 1, further comprising performing re-examinations at predetermined intervals to check whether bleeding is triggered in the regularly cleaned number of narrow interdental spaces, and providing a third interdental brush which has a third bristle area having a third outer contour with a uniform cylindrical cross-section from a proximal end of the third bristle area to a free end of the third bristle area, the third outer contour having a larger external diameter than a diameter of the second outer contour for the purposes of regular cleaning for the number of narrow interdental spaces which bleed when provoked.

3. The diagnostic method according to claim 1, wherein the first, conical interdental brush includes a handle and a wire element, which extends from the handle to the free end of the first, conical interdental brush, and to which the bristles are attached, the bristles decrease in length towards a free end of the wire element in at least one section, and a bristle-free section is formed at the free end of the wire element, and inserting the bristle-free section first into the narrow interdental space.

* * * * *